(12) United States Patent
De Moral et al.

(10) Patent No.: US 11,992,543 B2
(45) Date of Patent: May 28, 2024

(54) COSMETIC COMPOSITION

(71) Applicant: BEIERSDORF AG, Hamburg (DE)

(72) Inventors: Yanel De Moral, Silao Guanajuato (MX); Osvaldo Jose Fabian Cruz Cervantes, Silao Guanajuato (MX); Ana Karen Zavala Raya, Silao Guanajuato (MX)

(73) Assignee: BEIERSDORF AG, Hamburg (DE)

( * ) Notice: Subject to any disclaimer, the term of this patent is extended or adjusted under 35 U.S.C. 154(b) by 560 days.

(21) Appl. No.: 17/413,096

(22) PCT Filed: Aug. 10, 2020

(86) PCT No.: PCT/EP2020/072386
§ 371 (c)(1),
(2) Date: Jun. 11, 2021

(87) PCT Pub. No.: WO2022/033655
PCT Pub. Date: Feb. 17, 2022

(65) Prior Publication Data
US 2022/0323321 A1   Oct. 13, 2022

(51) Int. Cl.
| | | |
|---|---|---|
| *A61K 8/34* | (2006.01) |
| *A61K 8/06* | (2006.01) |
| *A61K 8/37* | (2006.01) |
| *A61K 8/73* | (2006.01) |
| *A61K 8/81* | (2006.01) |
| *A61K 8/891* | (2006.01) |
| *A61K 8/92* | (2006.01) |
| *A61Q 19/00* | (2006.01) |

(52) U.S. Cl.
CPC .............. *A61K 8/342* (2013.01); *A61K 8/062* (2013.01); *A61K 8/345* (2013.01); *A61K 8/37* (2013.01); *A61K 8/73* (2013.01); *A61K 8/8147* (2013.01); *A61K 8/891* (2013.01); *A61K 8/922* (2013.01); *A61Q 19/007* (2013.01)

(58) Field of Classification Search
None
See application file for complete search history.

(56) References Cited

U.S. PATENT DOCUMENTS

| | | |
|---|---|---|
| 4,216,201 A | 8/1980 | Calvo |
| 4,389,418 A | 6/1983 | Burton |
| 5,849,315 A | 12/1998 | Rerek et al. |
| 2006/0165741 A1* | 7/2006 | Coffindaffer ........... A61K 8/498 424/401 |

FOREIGN PATENT DOCUMENTS

WO    9850001 A1    11/1998

* cited by examiner

*Primary Examiner* — Dominic Lazaro
(74) *Attorney, Agent, or Firm* — Abel Schillinger, LLP

(57) ABSTRACT

The present invention belongs to the cosmetic field.

20 Claims, No Drawings

COSMETIC COMPOSITION

BACKGROUND OF THE INVENTION

1. Field of the Invention

The present invention belongs to a cosmetic composition to be used as nourishing body lotion, which moisturizes the skin without leaving a heavy barrier and a sticky feeling on the skin after application.

2. Discussion of Background Information

A beautiful and attractive appearance is a desire for many people. One typical sign of such an appearance is a healthy and smooth looking skin. Therefore, in order to take care on the skin, it is for many people a daily routine to apply cosmetic products such as body lotions, sunscreens or deodorant compositions.

Body lotions are usually used to moisten and restore the skin. Frequently, active substances are added to them, which regenerate the skin and, for example, prevent and reduce their premature aging (e.g. the development of wrinkles, wrinkles).

Conventional body lotions usually consist of emulsions. Emulsions are generally understood to mean heterogeneous systems which consist of two liquids which are immiscible or only to a limited extent miscible with one another, which are usually referred to as phases and in which one of the two liquids is dispersed in the form of very fine droplets in the other liquid.

Viewed externally and with the naked eye, emulsions appear homogeneous.

If the two liquids are water and oil and oil droplets are finely distributed in water, then it is an oil-in-water emulsion. The basic character of an O/W emulsion is characterized by the water. In a water-in-oil emulsion is the reverse principle, the basic character is determined by the oil here.

In order to prevent agglomeration effects in the emulsion emulsifier are usually added to the composition. An emulsifier is a substance that stabilizes an emulsion by increasing its kinetic stability. Emulsifiers are compounds that typically have a polar or hydrophilic (i.e. water-soluble) part and a non-polar (i.e. hydrophobic or lipophilic) part. Because of this, emulsifiers tend to have more or less solubility either in water or in oil. Emulsifiers that are more soluble in water (and conversely, less soluble in oil) will generally form oil-in-water emulsions, while emulsifiers that are more soluble in oil will form water-in-oil emulsions.

Also a number of body lotions in form of emulsions comprising emulsifier are disclosed in the document U.S. Pat. No. 4,216,201 A, WO1998050001A1 and U.S. Pat. No. 4,389,418A.

One aspect of most body lotions is that they leave a moisturizing film on the skin resulting in a comfortable soft skin feeling. In many cases, this film is perceived as sticky, especially if the film remains on the skin for many hours. However, more importantly, the film of leads to a barrier on the skin resulting in further disadvantages for the consumer.

For example, especially under warm conditions the barrier leads to an extra heating of the skin. Accordingly, the consumer feels less conformable. Furthermore, it is known from scientific disclosures that the cutaneous uptake of atmospheric oxygen contributes significantly to the oxygen supply of human dermis and epidermis (see M. Stücker et al.: *The cutaneous uptake of atmospheric oxygen contributes significantly to the oxygen supply of human dermis and epidermis*. In: *Journal of Physiology*. Band 538, 2002, Nr. 3, S. 985-994. PMID 11826181 doi:10.1113/jphysiol.2001.013067). Due to the presence of the described film the ability of the skin for cutaneous respiration is hindered. Accordingly the breathability of the skin is limited.

Thus, it remains desirable to provide cosmetic body lotion products which allow to moisturize the skin, but which do not exhibit at least some of the disadvantages described above.

It was surprisingly found by the applicant that these objectives can be addressed by the present invention.

SUMMARY OF THE INVENTION

The invention is a cosmetic oil in water emulsion comprising, based on the total weight of the emulsion,
  a) at least 72% by weight of water,
  b) 0.1 to 3% by weight of PPG-15 stearyl ether,
  c) 0.5 to 8% by weight of at least one oil selected from the group of C12-15 alkyl benzoate, isopropyl palmitate, isopropyl myristate and diisopropyl adipate, characterized in that the emulsion comprises further emulsifier in a total quantity of less than 0.5% by weight, more preferably less than 0.25% by weight, more preferably less than 0.1% by weight, whereby it is most preferred if the emulsion does not comprise further emulsifier.

A further object of the invention is the use of the emulsion according to the invention to moisturize the human skin without hindering the cutaneous respiration and/or the breathability of the human skin.

A further object of the invention is the use of the emulsion according to the invention to moisturize the human skin without significantly hindering the cutaneous respiration and/or the breathability of the human skin.

A further aspect of the invention is a method to moisturize the human skin without (significantly) hindering the cutaneous respiration and/or the breathability of the human skin characterized that the emulsion according to the invention is applied to the human skin.

The cosmetic emulsions according to the invention surprisingly allow for an effective moisturization of the human skin without forming a heavy, sticky barrier. Furthermore, it was surprisingly found that after application the emulsion the human skin is still able to exchange heat and/or air effectively with the environment. Accordingly, the emulsions allow the cutaneous respiration and/or the breathability of the human skin. Accordingly, a breathable nourishing body lotion can be provided. This breathable skin technology allows a body lotion to be provided, which also leaves the skin in a soft and smooth status with no sticky feeling. No heavy barrier is formed.

In the following description the terms "according to the invention", "preferred according to the invention" and so on are always directed to the use according to the invention, to the method according to the invention and to the cosmetic emulsion according to the invention.

All weight percentages (% by weight) given below relate, unless otherwise stated, to the total weight of the cosmetic emulsion. If ratios of certain components are disclosed in the following description, these ratios refer, unless otherwise stated, to weight ratios of the components.

Unless otherwise stated, all tests and measurements were performed under "normal conditions". The term "normal conditions" refers to 20° C., 1013 hPa and a relative humidity of 50%.

The term "after application" refers herein to a period of 12 hours, preferably 6 hours starting with the application of the cosmetic composition.

According to the invention oils generally are understood as water immiscible organic substances, which are liquid at 20° C. and 1013 hPa.

The term "skin" refers solely to human skin.

According to the present invention the emulsion comprises at least at least 72% by weight of water, calculated to the total weight of the emulsion. It is preferred if the total quantity of water is in the range from 73 to 90% by weight, more preferably 75 to 88% by weight and most preferably 77 to 86% by weight calculated to the total weight of the composition.

Furthermore, the emulsion of the present invention is characterized in that the emulsion comprises 0.1 to 3% by weight of PPG-15 stearyl ether. It is preferred if the total quantity of PPG-15 stearyl ether is in the range from 0.2 to 2% by weight, more preferably 0.4 to 1.5% by weight and most preferably 0.6 to 1% by weight, calculated to the total weight of the emulsion.

In addition to that, the emulsion is characterized in that it comprises 0.5 to 8% by weight of at least one oil selected from the group of C12-15 alkyl benzoate, isopropyl palmitate, isopropyl myristate and diisopropyl adipate.

According to the invention it is preferred if at least C12-15 alkyl benzoate is contained.

For the case that C12-15 alkyl benzoate is contained, it is preferred if the total quantity of C12-15 alkyl benzoate is in the range from 0.5 to 8% by weight, more preferably from 2 to 6.5% by weight and most preferably from 3 to 5% by weight, calculated to the total weight of the emulsion.

Further it is preferred in some embodiments of the invention, if isopropyl myristate and/or isopropyl palmitate are contained. For the case that isopropyl myristate and/or isopropyl palmitate are contained, it is preferred if the total quantity of both ingredients is in the range from 0.2 to 5% by weight, more preferably from 0.5 to 4% and most preferably 1% to 3% by weight, calculated to the total weight of the emulsion.

It is well known to the person skilled in art that PPG-15 stearyl ether, isopropyl myristate and isopropyl myristate are considered as oils. Accordingly, they are situated in the oil phase of the emulsion.

According to the invention it is preferred if at least diisopropyl adipate is contained.

For the case that diisopropyl adipate is contained, it is preferred if the total quantity of diisopropyl adipate is in the range from 0.5 to 8% by weight, more preferably from 2 to 6.5% by weight and most preferably from 3 to 5% by weight, calculated to the total weight of the emulsion.

Further, it is preferred if the emulsion comprises 0.1 to 0.5% by weight of at least one non-volatile silicone oil, based on the total weight of the emulsion. It is preferred if the non-volatile silicone oil is dimethicone.

Further, it is preferred if the emulsion comprises Butyrospermum Parkii (Shea) Butter. For the case that Butyrospermum Parkii (Shea) Butter is contained, it is further preferred if the total quantity of Butyrospermum Parkii (Shea) Butter is in the range from 0.1 to 1.5% by weight, more preferably 0.4 to 1% by weight, calculated to the total weight of the emulsion.

Furthermore, it is preferred if the emulsion comprises at least one fatty alcohol containing 14 to 22 carbon atoms. Preferred fatty alcohols to be contained in the emulsion are cetearyl alcohol and/behenyl alcohol. For the case that at least one fatty alcohol containing 14 to 22 carbon atoms is contained in the emulsion, it is further preferred if the total quantity of those fatty alcohols is in the range from 0.3 to 3% by weight, more preferably 1 to 2.5% by weight and most preferably 1.25 to 2.25% by weight, calculated to the total weight of the emulsion.

Fatty alcohols containing 14 to 22 carbon atoms are considered as part of the oil phase.

According to the invention, it is preferred if the total quantity of the oil phase is in the range from 5 to 15% by weight, more preferably from 6% to 12% by weight and most preferred from 7% to 11% by weight, calculated to the total weight of the emulsion. Further emulsifier, if present, do not count to the oil phase of the cosmetic emulsion.

Further, it is preferred according to the invention if the emulsion comprises at least one gel forming polymer. A gel forming polymer is considered as a polymer which forms a gel network in the emulsion according to the invention. For the case a gel forming polymer is contained, it is preferred if the total quantity of the gel forming polymer is in the range from 0.1 to 1% by weight calculated to the total weight of the emulsion.

Particular preferred gel forming polymers are acrylates/C10-30 alkyl acrylate crosspolymer and/or xanthan gum. Accordingly, it is preferred if acrylates/C10-30 alkyl acrylate crosspolymer and/or xanthan gum are contained. For the case that acrylates/C10-30 alkyl acrylate crosspolymer and/or xanthan gum are contained, it is further preferred if the total quantity of acrylates/C10-30 alkyl acrylate crosspolymer and/or xanthan gum is in the range from 0.1 to 1% by weight, more preferably 0.25 to 0.8% by weight and most preferably 0.4 to 0.6% by weight, calculated to the total weight of the emulsion.

According to the invention, it is further preferred if the cosmetic emulsion contains phenoxyethanol. In the case the cosmetic emulsion contains phenoxyethanol the total quantity of phenoxyethanol is preferably in the range from 0.1% by weight to 2% by weight and more preferably from 0.4% by weight to 1% by weight, calculated to the total weight of the emulsion.

Moreover, preferred cosmetic emulsions of the present invention are therein characterized that they contain ethylhexylglycerin, whereby it is further preferred if the total quantity of ethylhexylglycerin is in the range from 0.05% to 0.5% by weight, calculated to the total weight of the emulsion.

Furthermore, it is preferred if the emulsion does not contain an alkylparabene such as methyl parabene and/or butyl parabene.

Moreover, it is preferred according to the present invention if the cosmetic emulsion contains polymers which are polymerized from a mixture containing polyols and di- or poly-isocyanate in a total quantity of 0% by weight, calculated to the total weight of the emulsion.

Further preferred cosmetic compositions according to the invention contain glycerol in a total quantity from 1% to 12%, more preferably from 2% to 10% by weight calculated to the total weight of the emulsion.

In addition, preferred cosmetic emulsions are characterized in that they contain ethanol in a total quantity of less than 0.5% by weight, more preferably less than 0.2% by weight and most preferably 0% by weight, calculated to the total weight of the emulsion.

According to the invention the cosmetic emulsion may preferably contains at least one compound selected from the group of limonene, linalool, citral, alpha-isomethyl ionone and geraniol.

Other preferred emulsions of the invention are characterized in that that they do not contain compounds selected from the group of limonene, linalool, citral, alpha-isomethyl ionone and geraniol.

Moreover, it is further preferred if the cosmetic emulsion according to the invention has a pH value in the range from 4.5 to 8, preferably from 5.5 to 7.0 and most preferred from 6.0 to 6.7.

Additionally, preferred cosmetic emulsions of the present invention are therein characterized that they have a viscosity in the range from 3000 mPas to 8000 mPas, whereby the viscosity is measured using a Brookfield RV viscometer, spindle RV 4, 20 rpm without Helipath, at 20° C. ambient temperature and 20° C. sample temperature.

Furthermore, it is advantageous according to the invention if the cosmetic emulsion contains one or more compounds selected from the group of alpha-lipoic acid, folic acid, phytoene, D-biotin, tocopherol, coenzyme Q10, alpha-glucosylrutin, carnitine, carnosine, natural and/or synthetic isoflavonoids, flavonoids, creatine, creatinine, taurine, β-alanine, tocopheryl acetate, dihydroxyacetone, glycyrrhetinic acid, 8-hexadecene-1, 16-dicarboxylic acid, glycerylglycose, (2-hydroxyethyl) urea and/or licochalcone A.

In the case the cosmetic emulsion comprises at least one oil phase and at least one aqueous phase it is generally preferred, if at least one oil phase is dispersed in an aqueous phase.

DETAILED DESCRIPTION OF EXEMPLARY EMBODIMENTS OF THE INVENTION

Examples:

The following examples should illustrate the compositions of this invention, without intending to limit the invention to these examples. The numerical values in the examples are percentages by weight, based on the total weight of the preparations.

EXAMPLES

| Ingredients | Ex. 1 | Ex. 2 | Ex. 3 | Ex. 4 | Ex. 5 |
|---|---|---|---|---|---|
| Ethylhexylglycerin | 0.2 | 0.2 | 0.2 | 0.2 | 0.2 |
| Butyrospermum Parkii Butter | 0.8 | 0.8 | 0.8 | 0.8 | 0.8 |
| Dimethicone | 0.3 | 0.3 | 0.3 | 0.3 | 0.3 |
| PPG-15 Stearyl Ether | 0.7 | 0.7 | 0.7 | 0.7 | 0.7 |
| C12-15 Alkyl Benzoate | 4 | 4 | 4 | 4 | 4 |
| Isopropyl myristate | | 2 | | | |
| Isopropyl Palmitate | | | 2 | | |
| Acrylates/C10-30 Alkyl Acrylate Crosspolymer | 0.5 | 0.5 | 0.5 | 0.5 | 0.5 |
| Parfum (containing limonene, linalool, citral, citronellol and/or alpha-isomethyl ionone | 0.35 | 0.35 | 0.35 | 0.35 | 0.35 |
| Glycerin | 5 | 9 | 8 | 6 | 7 |
| Sodium Hydroxide | 0.15 | 0.15 | 0.15 | 0.15 | 0.15 |
| Phenoxyethanol | 0.9 | 0.9 | 0.9 | 0.9 | 0.9 |
| Cetearyl alcohol | 1.5 | 1.5 | 1.5 | 1.5 | 1.5 |
| Aqua | ad 100 | ad 100 | ad 100 | ad 100 | ad 100 |

Example Ex.1 was compared to a commercial product, known under the Product name Nivea repair and care, which has the following INCI: aqua, glycerin, C15-19 alkane, isopropyl palmitate, cetearyl alcohol, dimethicone, glyceryl stearate SE, panthenol, glyceryl stearate, myristyl alcohol, cera microcristallina, hydrogenated coco-glycerides, paraffinum liquidum, carbomer, sodium cetearyl sulfate, sodium hydroxide, ethylhexylglycerin, phenoxyethanol, linalool, benzyl alcohol, parfum.

The formulas were compared by applying 100 µl of each formula on two separate square section (size: 8 cm×5 cm) on the back, namely one on each side net to the spine, of a human body. After application (5 minutes) it was evaluated how much residue was found to be left. The rating was in the range from—meaning low amount of residue—to 5—high amount of residue. Furthermore, the absorption speed was analyzed by comparing both sections.

In this first set of experiments it was found that the score for the residue for Ex.1 was 2.0 while the commercial had a worse score with 2.3. Furthermore, it was noticed that Ex.1 absorbed significantly faster than the commercial product.

Afterwards, the participants in the study were ask to start cycling for 15 minutes. While workout the back of the participants were monitored using a thermal imaging camera. After the workout it was found that the skin surface temperature of the section treated with Ex.1 was in average 2° C. lower than the one treated with the commercial product. The barrier formed commercial product leads to a heating up of the skin which is not desirable. No barrier was formed in the section treated with Ex.1 such that heat can be released to the environment. Accordingly, without the barrier the cutaneous respiration and/or the breathability of the human skin is not hindered, while a moisturization effect of the skin is achieved. Both products were perceived by the participants to moisturize the skin sufficiently.

Further examples:

| Ingredients | Ex. 1 | Ex. 2 | Ex. 3 | Ex. 4 | Ex. 5 |
|---|---|---|---|---|---|
| Ethylhexylglycerin | 0.2 | 0.2 | 0.2 | 0.2 | 0.2 |
| Butyrospermum Parkii Butter | 0.8 | 0.8 | 0.8 | 0.8 | 0.8 |
| Dimethicone | 0.3 | 0.3 | 0.3 | 0.3 | 0.3 |
| PPG-15 Stearyl Ether | 0.7 | 0.7 | 0.7 | 0.7 | 0.7 |
| C12-15 Alkyl Benzoate | | | 4 | 4 | 2 |
| Isopropyl myristate | | 2 | | | 1 |
| Isopropyl Palmitate | | | 2 | 2 | 1 |
| Diisopropyl Adipate | 4 | | | | 1 |
| Acrylates/C10-30 Alkyl Acrylate Crosspolymer | 0.5 | | 0.4 | | |
| Xanthan Gum | | 0.3 | | 0.25 | 0.4 |
| Parfum (containing limonene, linalool, citral, citronellol and/or alpha-isomethyl ionone | 0.35 | 0.35 | 0.35 | 0.35 | 0.35 |
| Glycerin | 5 | 9 | 8 | 6 | 7 |
| Sodium Hydroxide | 0.15 | 0.15 | 0.15 | 0.15 | 0.15 |
| Phenoxyethanol | 0.9 | 0.9 | 0.9 | 0.9 | 0.9 |
| Cetearyl alcohol | 1.5 | 1.5 | 1.5 | 1.5 | 1.5 |
| Aqua | ad 100 | ad 100 | ad 100 | ad 100 | ad 100 |

What is claimed is:

1. A cosmetic oil-in-water (O/W) emulsion, wherein the emulsion comprises, based on a total weight of the emulsion,
    (a) at least 72% by weight of water,
    (b) from 0.1 to 3% by weight of PPG-15 stearyl ether,
    (c) from 0.5 to 8% by weight of at least one oil selected from C12-15 alkyl benzoate, isopropyl palmitate, isopropyl myristate and diisopropyl adipate,
and wherein the emulsion comprises a total of from 0% to less than 0.5% by weight of one or more further emulsifiers.

2. The emulsion of claim 1, wherein the emulsion comprises a total of 0% to less than 0.1% by weight of one or more further emulsifiers.

3. The emulsion of claim 1, wherein the emulsion does not comprise any further emulsifier.

4. The emulsion of claim 1, wherein the emulsion comprises from 73% to 90% by weight of water.

5. The emulsion of claim 1, wherein the emulsion comprises from 77% to 86% by weight of water.

6. The emulsion of claim 1, wherein the emulsion comprises from 0.2% to 2% by weight of PPG-15 stearyl ether.

7. The emulsion of claim 1, wherein the emulsion comprises from 0.4% to 1.5% by weight of PPG-15 stearyl ether.

8. The emulsion of claim 1, wherein the emulsion comprises from 0.5% to 8% by weight of C12-15 alkyl benzoate.

9. The emulsion of claim 1, wherein the emulsion comprises a total of from 0.2% to 5% by weight of isopropyl myristate and/or isopropyl palmitate.

10. The emulsion of claim 1, wherein the emulsion comprises from 0.5% to 8% by weight of diisopropyl adipate.

11. The emulsion of claim 1, wherein the emulsion further comprises from 0.1% to 0.5% by weight of at least one non-volatile silicone oil.

12. The emulsion of claim 1, wherein the emulsion further comprises Butyrospermum Parkii (Shea) Butter.

13. The emulsion of claim 1, wherein the emulsion further comprises at least one fatty alcohol containing from 14 to 22 carbon atoms.

14. The emulsion of claim 1, wherein a total concentration of an oil phase of the emulsion is from 5% to 15% by weight, based on the total weight of the emulsion.

15. The emulsion of claim 1, wherein a total concentration of an oil phase of the emulsion is from 7% to 11% by weight, based on the total weight of the emulsion.

16. The emulsion of claim 1, wherein the emulsion further comprises at least one gel forming polymer.

17. The emulsion of claim 1, wherein the emulsion further comprises acrylates/C10-30 alkyl acrylate crosspolymer and/or xanthan gum.

18. The emulsion of claim 1, wherein the emulsion further comprises from 1% to 12% by weight of glycerol.

19. The emulsion of claim 1, wherein the emulsion has a pH of from 4.5 to 8.

20. A method of moisturizing human skin without significantly hindering the cutaneous respiration and/or the breathability of the human skin, wherein the method comprises applying to the human skin the emulsion of claim 1.

* * * * *